US00PP19613P2

(12) United States Plant Patent
Vlielander

(10) Patent No.: US PP19,613 P2
(45) Date of Patent: Jan. 6, 2009

(54) ***KALANCHOE* PLANT NAMED 'KALUNA'**

(50) Latin Name: *Kalanchoe blossfeldiana*
Varietal Denomination: Kaluna

(76) Inventor: Ike J. Vlielander, De Lier (NL)

( * ) Notice: Subject to any disclaimer, the term of this patent is extended or adjusted under 35 U.S.C. 154(b) by 0 days.

(21) Appl. No.: 12/012,489

(22) Filed: Jan. 31, 2008

(51) Int. Cl.
*A01H 5/00* (2006.01)

(52) U.S. Cl. ..... Plt./341

(58) Field of Classification Search ..... Plt./341
See application file for complete search history.

*Primary Examiner*—Kent L. Bell
*Assistant Examiner*—Georgia Helmer

(57) ABSTRACT

A new and distinct cultivar of *Kalanchoe* plant named 'Kaluna', characterized by its compact, upright and uniform growth habit; freely branching plant habit; dark green-colored leaves; uniform, freely and early flowering habit; red-colored flowers; and excellent postproduction longevity.

1 Drawing Sheet

Botanical Designation: *Kalanchoe blossfeldiana.*
Cultivar Denomination: 'KALUNA'.

BACKGROUND OF THE INVENTION

The present invention relates to a new and distinct cultivar of *Kalanchoe*, botanically known as *Kalanchoe blossfeldiana*, and hereinafter referred to by the name 'Kaluna'.

The new *Kalanchoe* is a naturally-occurring whole plant mutation of the *Kalanchoe blossfeldiana* cultivar Kawi, not patented. The cultivar 'Kaluna' was discovered and selected by the Inventor as a flowering plant from within a population of plants of the cultivar Kawi in a controlled greenhouse environment in De Lier, The Netherlands in 2002.

Asexual reproduction of the new *Kalanchoe* by vegetative terminal cuttings in a controlled environment in De Lier, The Netherlands since 2002, has shown that the unique features of this new *Kalanchoe* are stable and reproduced true to type in successive generations.

SUMMARY OF THE INVENTION

The cultivar 'Kaluna' has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kaluna'. These characteristics in combination distinguish 'Kaluna' as a new and distinct cultivar of *Kalanchoe:*

1. Compact, upright and uniform growth habit.
2. Freely branching plant habit.
3. Dark green-colored leaves.
4. Uniform, freely and early flowering habit.
5. Red-colored flowers.
6. Excellent postproduction longevity.

Plants of the new *Kalanchoe* can be compared to plants of the parent, the cultivar Kawi. Plants of the new *Kalanchoe* differ from plants of the cultivar Kawi in the following characteristics:

1. Plants of the new *Kalanchoe* are more compact than plants of the cultivar Kawi.
2. Plants of the new *Kalanchoe* have smaller leaves than plants of the cultivar Kawi.
3. Plants of the new *Kalanchoe* have slightly smaller flowers than plants of the cultivar Kawi.
4. Plants of the new *Kalanchoe* and the cultivar Kawi differ in flower color as plants of the cultivar Kawi have pinkish red-colored flowers.

Plant of the new *Kalanchoe* can be compared to plants of the *Kalanchoe blossfeldiana* cultivar Kerinci, disclosed in U.S. Plant Pat. No. 10,031. In side-by-side comparisons conducted in De Lier, The Netherlands, plants of the new *Kalanchoe* differed from plants of the cultivar Kerinci in the following characteristics:

1. Plants of the new *Kalanchoe* were not as vigorous as plants of the cultivar Kerinci.
2. Plants of the new *Kalanchoe* had smaller leaves than plants of the cultivar Kerinci.
3. Plants of the new *Kalanchoe* had smaller flowers than plants of the cultivar Kerinci.
4. Plants of the new *Kalanchoe* and the cultivar Kerinci differed in flower color as plants of the cultivar Kerinci had pink-colored flowers.

BRIEF DESCRIPTION OF THE PHOTOGRAPH

The accompanying colored photograph illustrates the overall appearance of the new *Kalanchoe*, showing the colors as true as it is reasonably possible to obtain in colored reproductions of this type. Colors in the photograph my differ slightly from the color values cited in the detailed botanical description which accurately describe the colors of the new *Kalanchoe*. The photograph comprises a side perspective view of a typical flowering plant of 'Kaluna' grown in a container.

DETAILED BOTANICAL DESCRIPTION

The aforementioned photograph and following observations, measurements and values describe plants grown in De Lier, The Netherlands in a glass-covered greenhouse during the autumn and under conditions which closely approximate commercial production. During the production of the plants, day and night temperatures ranged from 19° C. to 26° C., night temperatures ranged from 20° C. to 21° C. and light levels ranged from 10,000 lux to 60,000 lux. Unrooted cuttings were directly stuck in 10-cm containers and received long day/short night conditions (more than 14 hours of light) for about four weeks; plants then received photoinductive short day/long night conditions (minimum 14 hours darkness) until flowering. Plants were about 16 weeks old when the photograph and the description were taken. In the detailed description, color references are made to The Royal Horticutural Society Colour Chart, 1995 Edition, except where general terms of ordinary dictionary significance are used.

Botanical classification: *Kalanchoe blossfeldiana* cultivar 'Kaluna'.

Parentage: Naturally-occurring whole plant mutation of the *Kalanchoe blossfeldiana* Kawi, not patented.

Propagation:

*Type.*—By vegetative terminal cuttings.

*Time to initiate roots, summer.*—About ten days at temperatures of 21° C.

*Time to initiate roots, winter.*—About 14 days at temperatures of 21° C.

*Time to produce a rooted young plant, summer.*—About three weeks at temperatures of 21° C.

*Time to produce a rooted young plant, winter.*—About four weeks at temperatures of 21° C.

*Root description.*—Fine, fibrous; greyish white in color.

*Rooting habit.*—Freely branching; dense.

Plant Description:

*Plant habit.*—Compact, upright and uniform growth habit. Very freely flowering with numerous compound cymes. Inverted triangle with rounded crown. Appropriate for 10-cm to 15-cm containers. Moderately vigorous growth habit.

*Plant height at flowering.*—About 20 cm.

*Plant diameter at flowering.*—About 16 cm.

*Branching habit.*—Freely branching, usually about seven to nine lateral branches develop per plant. Pinching (removal of the terminal apex) is not required but will enhance lateral branch development.

Lateral Branch Description:

*Length.*—About 13 cm to 17 cm.

*Diameter.*—About 3 mm to 6 mm.

*Internode length.*—About 2 cm to 4 cm.

*Aspect.*—Erect.

*Strength.*—Moderately strong.

*Texture.*—Smooth, glabrous.

*Color.*—137A.

Foliage Description:

*Arrangement.*—Opposite, simple; generally symmetrical.

*Quantity per plant.*—About 10 to 15 mature leaves and about 16 to 25 generative leaves.

*Length.*—About 9.5 cm.

*Width.*—7.5 cm.

*Shape.*—Elliptic.

*Apex.*—Acute to obtuse.

*Base.*—Acute.

*Margin.*—Crenate.

*Texture, upper and lower surfaces.*—Smooth, glabrous, leathery; succulent.

*Venation pattern.*—Pinnate.

*Color.*—Developing and fully developed foliage, upper surface: 137A; venation, 137A to 137B. Developing and fully developed foliage, lower surface: 137B.

*Petiole.*—Length: About 1.6 cm. Diameter: About 4 mm to 8 mm. Texture, upper and lower surfaces: Smooth glabrous. Color, upper and lower surfaces: Between 147A to 147B and 137A.

Flower Description:

*Flower arrangement and habit.*—Flowers arranged singly in compound dichasial cymes that arise from leaf axils. Uniform and freely flowering habit with usually about 25 open flowers and about 25 flower buds per lateral branch and more than 200 open flowers and flower buds per plant. Flowering continuously for at least seven weeks. Flowers persistent. Flowers not fragrant. Natural flowering season: Plants of the new *Kalanchoe* initiate and develop flowers under short day/long night conditions or during the late autumn/winter/early spring. Flower initiation and development can also be induced under artificial short day/long conditions (at least 14 hours of darkness).

*Time to flower.*—Early flowering habit; under short day/long night photoinductive conditions, about eight to twelve weeks are required. Actual time to flower is primarily dependent upon temperature and light intensity.

*Post-production longevity.*—Excellent post-production longevity; plants maintain good foliage and flower substance for about 45 days under interior environmental conditions. Individual flowers last about 20 days on the plant.

*Flower diameter.*—About 1.6 cm.

*Flower length (height).*—About 1.4 cm.

*Flower bud.*—Shape: Initially oblong, becoming tubular ovoid with development. Length: About 9 mm. Diameter: About 2.5 mm. Color: 138C; becoming closer to 49D with development.

*Petals.*—Arrangement: Four fused at the base. Length: About 8 mm. Width: About 5 mm. Aspect: Flat to partially upright. Shape: Ovate. Apex: Acute. Margin: Entire. Texture, upper and lower surfaces: Smooth, glabrous. Color: When opening, upper surface: 46A. When opening, lower surface: 46B. Fully opened, upper surface: 46C; color becoming closer to 46D with development. Fully opened, lower surface: Between 49A and 50D.

*Sepals.*—Appearance: Four fused at the base. Length: About 6 mm. Width: About 2.5 mm. Shape: Oblong, pointed. Apex. Acute. Base. Obtuse. Margin: Entire. Aspect: Upright. Texture, upper and lower surfaces: Smooth; glabrous. Color, upper and lower surfaces: 138D.

*Peduncles.*—Length: About 3 mm to 5 mm. Diameter: About 1 mm. Aspect: Erect. Strength: Strong. Texture: Smooth, glabrous. Color: 138B.

*Reproductive organs.*—Androecium: Stamen number: About eight per flower. Anther shape: Elliptic, flat. Anther length: About 0.3 mm. Anther color: Color to 150D. Amount of pollen: Scarce. Pollen color: Close to 12A. Gynoecium: Pistil number: About four per flower. Pistil length: About 1 cm. Style length: About 1 mm. Style color: 138D. Stigma shape: Flat. Stigma color: 8D. Ovary color: 138D.

*Seed.*—Length: About 0.1 mm. Diameter: About 0.05 mm. Color: Close to 166C.

Temperature Tolerance: Plants of the new *Kalanchoe* have been observed to tolerate temperatures from about 12° C. to about 35° C.

Pathogen/Pest Resistance: Plants of the new *Kalanchoe* have not been observed to be resistant to pests and pathogens common to *Kalanchoes*.

It is claimed:

1. A new and distinct *Kalanchoe* plant named 'Kaluna ' as illustrated and described.

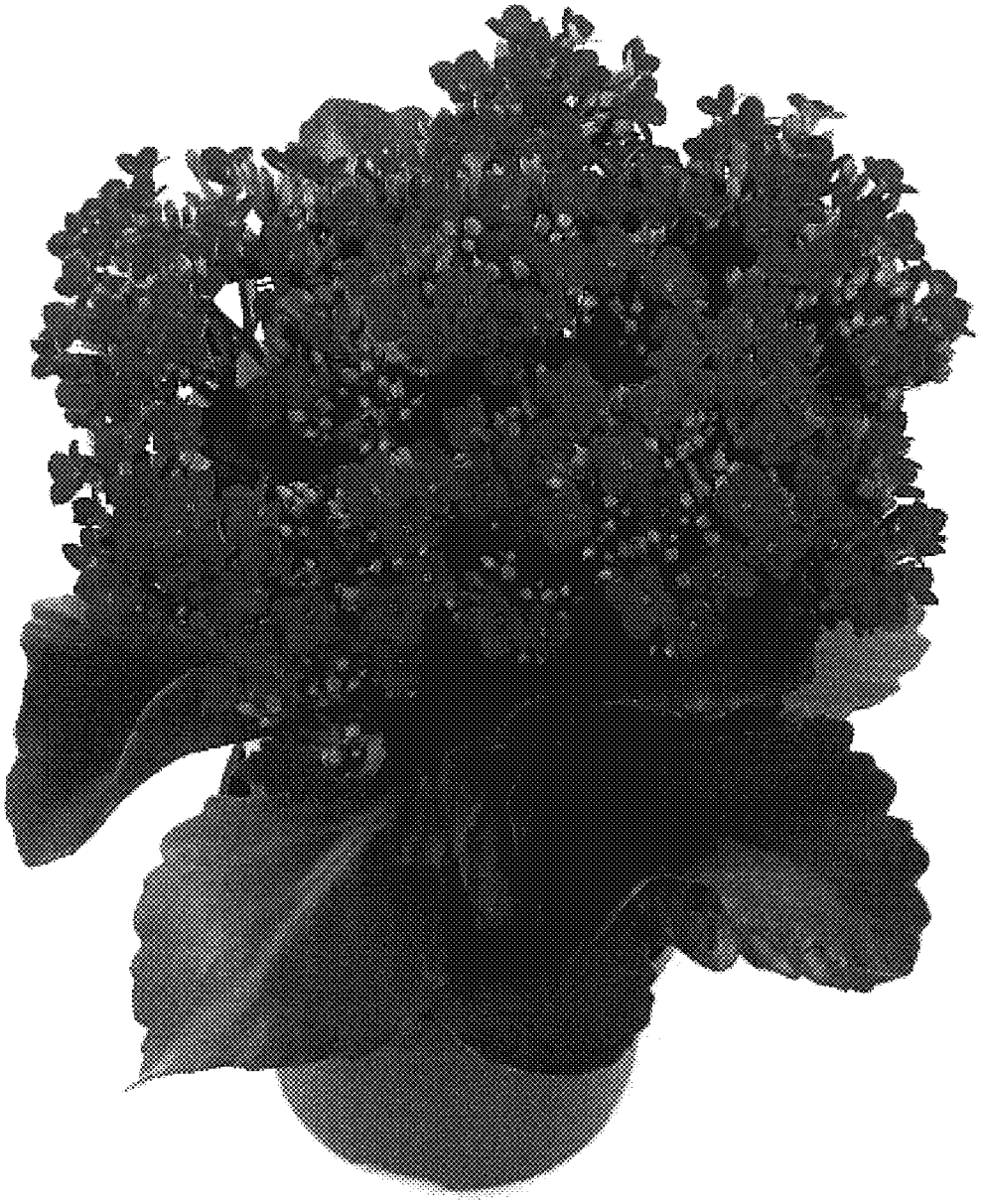

* * * * *